United States Patent [19]

Kerschensteiner

[11] Patent Number: 5,310,647

[45] Date of Patent: May 10, 1994

[54] DETECTION AND MEASUREMENT OF DESTRUCTIVE AND POLYMER FORMING ENZYMES BY COLLOIDAL FLOCCULATION

[75] Inventor: Daniel A. Kerschensteiner, Chester County, Pa.

[73] Assignee: Cherrystone Corporation, Wayne, Pa.

[21] Appl. No.: 861,654

[22] Filed: Apr. 1, 1992

[51] Int. Cl.$^5$ .......................... C12Q 1/00; C12Q 1/37
[52] U.S. Cl. .......................................... 435/4; 435/23; 435/962; 436/811
[58] Field of Search .................... 435/4, 23, 810, 962, 435/975; 436/808, 811

[56] References Cited

U.S. PATENT DOCUMENTS

| | | | |
|---|---|---|---|
| 4,164,558 | 8/1979 | von Schulthess | 424/12 |
| 4,313,734 | 2/1982 | Leuvering | 23/230 B |
| 4,859,612 | 8/1989 | Cole | 436/523 |
| 5,108,933 | 4/1992 | Liberti | 436/501 |
| 5,120,643 | 6/1992 | Ching | 435/7.92 |

OTHER PUBLICATIONS

Vitto, Veli-Jukka, "Human Gingival Proteases"—Journal of Periodontal Research, 22: pp. 58-63 (1987).
Gangbar, G., Overall, C. M., McCullough, C. A. G., Sodek, J., "Identification of Polymorphonuclear Leucocyte Collaganese and Gelatanase Activity in Mouthrinse Samples"—J. Periodontal Res., 25—pp. 257-267 (1990).
Fleer, G. J. and Lyklema J. Polymer—"Adsorption and Its Effect on the Stability of Hydrophobic Colloids'-'—J. Colloid and Interfacial Sci.—p. 46 (Jan. 1974).
Vitto, V.—J., Suomalainen, K. Sorsa, T., "Salivary Collaganese", J. Periodontal Res., 25, pp. 135-142 (1990).
Vitto, V. J., Tryggusaon et al.—"Collagen Enzymes in Periodontal Disease"; Proc. Finn. Dent. Soc., 83, pp. 119-129 (1987).
Scheie, A. A. et al.; "Polysaccharide Production by Cell Free Transferases in Saliva in Relation to Salivary Microflora"—Scand. J. Dent. Res., 92; 43-49 (1984).
Scheie, A. A. et al., "Cell-Free Glucosyltransferase in Saliva", Caries Res., 20—pp. 344-348 (1986).
Buchan, R. J. et al.—"Glucosyltransferase Production by Streptococcus Sanguis Challis and Comparison with Other Oral Streptococci"—Oral Microbiol Immunol., 5—pp. 63-71 (1990).

(List continued on next page.)

Primary Examiner—Michael G. Wityshyn
Assistant Examiner—Ralph Gitomer
Attorney, Agent, or Firm—Allan Jacobson; Gerry J. Elman; Sadhir G. Deshmukh

[57] ABSTRACT

The change between a dispersed state and a flocculated state of a colloidal agent (e.g. Congo Rubin, colloidal gold) is used to provide sensitive visual detection and optionally assay of enzyme in a sample. The test cell includes a substrate for the enzyme, and, depending on the action of the enzyme, polymer which protects the colloid from electrolyte-induced flocculation is either formed or destroyed by the test reaction. In a test for a hydrolytic enzyme (e.g. a protease) the colloid loses protection and flocculates. In a test for a polymer-forming enzyme, the colloid gains protection and is prevented from flocculating by added electrolyte, or alternatively, depending on the polymer's behavior, becomes more sensitive to the flocculating action of the added electrolyte. The measurement may be quantitated using an instrumental monitor. The test uses a natural substrate for the enzyme to be assayed (e.g., gelatin for the gelatinase class of enzymes) and may achieve rapid speed. The test may be performed using a biologically-derived sample for diagnostically relevant purposes, e.g. to detect an enzyme indicative of periodontal disease. A kit for performing the test is also disclosed.

7 Claims, No Drawings

OTHER PUBLICATIONS

Dibdin, G. H., et al., "Physical and Biochemical Studies of Streptococcus Mutans Sediments Suggest New Factors Linking the Cariogenicity of Plaque and its Extracellular Polysaccharide Content"—J. Dental Research, 67(6)—pp. 890∝895 (1988).

Frens, G., "Controlled Nucleation for the Regulation of the Particular Size in Monodisperse Gold Suspensions'"—Nature Physical Science—pp. 20-22 (Jan. 1973).

Kraugh, A. M., et al.—Photographic Sci., 15—pp. 220-225 (1980).

Makinen, K. K., et al.—"Benzoylarginine Peptidase and Iminopeptidase Profiles . . . "—Current Microbiology[1-4]—pp. 85-89 (1986).

Kasten, M. et al., Anal Biochem., 176, pp. 150-156 (1989).

Ciamasori, G. et al.—"Proteinases of the Gingival Crevice and Their Inhibitors"—Academic Press, 1980—pp. 31-49.

Fleer, C. J. et al., "Polymar Adsorption and Its Effection Stability of Hydrophobic Colloids"—J. of Colloid and Interfacial Sci., 16—pp. 1-12, (Jan. 1974).

DETECTION AND MEASUREMENT OF DESTRUCTIVE AND POLYMER FORMING ENZYMES BY COLLOIDAL FLOCCULATION

FIELD OF THE INVENTION

The present invention relates to a colloidal flocculation test for the detection of an enzyme and to a diagnostic test kit for use in the detection of an enzyme.

BACKGROUND

The present invention provides means for the detection of hydrolytic enzymes and of polymer-forming enzymes. Elastase is an example of a hydrolytic enzyme. It is an endopeptidase which will digest or cleave a wide variety of protein substrates. It is conventionally assayed by any of several methods involving the measurement of the amount of insoluble elastin substrate solubilized by enzyme digestion. The most convenient assays are those which involve the colorimetric determination of the amount of dye released into solution from digestion of dyed elastin substrates such as Congo Red-elastin, azoelastin, and orcein-elastin.

The Congo Red-elastin method of Naughton and Sanger is a use of fibrin dyed with Congo Red to measure general proteolytic activity. This procedure involves the use of a thoroughly dyed preparation of the substrate elastin. The colored solution that results from the reaction must be separated and subsequently measured, since it is the same color as the starting material. It would be desirable to provide a different means for detection, whereby, as in the present invention, a positive result produces a visibly detected color change not requiring separation.

Glucosyltransferase (GTF) is an example of a polymer-forming enzyme: it catalyzes the synthesis of water-soluble and water insoluble long chain polymers from the substrate sucrose (Buchan et al., Dibdin and Shellis). One method of detecting this enzyme is by using radioactively-labeled sucrose. Reacting this with GTF, any water soluble polymer product which forms is adsorbed onto filter paper separate from the sucrose substrate. The amount of radioactivity incorporated into polymer is measured by conventional scintillation counting. Water insoluble polysaccharide product is measured instrumentally by the measurement of turbidity in a clear solution containing sucrose and the enzyme, or alternatively by measuring the incorporation of radioactivity into polymer which adheres to the sides of an inclined glass test tube containing radiolabeled sucrose and glucosyltransferase.

There are various agglutination assays that use a flocculating colloid to indicate the result. One example is the polystyrene latex agglutination test. An aggregation of polystyrene latex colloidal particles occurs when adsorbed or coupled antibody attached to the particles' surface reacts with antigen in an aqueous sample (U.S. Pat. No. 4,164,558). Another example (U.S. Pat. No. 4,313,734) employs colloidal metal sols to produce a color change. However, these agglutination assays are based on ligand binding and do not provide a means for detecting an enzyme.

Using bovine serum albumin (BSA) and gelatin, a melted, denatured form of collagen, and Congo Red, a colloidal dyestuff, I discovered that high concentrations of BSA or gelatin tend to protect colloidal dyes from flocculation by a concentration of simple salts-sodium or potassium chloride-which ordinarily would have flocculated had the BSA or gelatin not been added. This is an example of colloidal protection.

Protection, Unprotection and Sensitizing Principles

When an electrolyte (e.g. salt) solution is added to an aqueous colloidal dispersion of a colloid, the colloid will flocculate. The colloid in this instance is unprotected to the action of the electrolyte solution. If a high concentration of a polymer, such as gelatin is added to the colloidal dispersion, it becomes resistant to the flocculating effect of the electrolyte-the colloid is considered protected.

With selected polymers, gelatin in particular, reducing its concentration below that determined to be protective, a sensitizing action sometimes results, whereupon colloidal flocculation occurs in the presence of an ionic strength which ordinarily would not cause flocculation. These three conditions of polymer acting upon colloidal behavior in the presence of electrolyte-protection, unprotection, and sensitization-are the physical-chemical phenomena upon which the invention is based.

Summary of the Actions of a Protective Polymer and Electrolyte with Colloids

| Unprotective → Sensitizing → Protective | | |
|---|---|---|
| POLYMER CONCENTRATION | | |
| Low or None | Intermediate | High |
| RESPONSE TO ELECTROLYTE | | |
| Flocculate | Easiest to Flocculate | Unresponsive |

A Protection-Unprotection Example

An example of a protection-deprotection phenomenon involves the detection of a protease. In this example, a colloidal dispersion is protected from salt flocculation by the addition of a protecting amount of gelatin. Introducing a protease such trypsin to this system of colloid, gelatin and electrolyte causes flocculation of the colloidal suspension by virtue of the enzyme's action in reducing the size of the polymeric protein through hydrolytic cleavage. As a result of this action, the colloidal suspension is left unprotected to the flocculating action of the electrolyte. The results are identical if the enzyme action produces a sensitizing condition as a result of incomplete destruction of the protein, in place of an unprotected condition caused by complete destruction. Thus a flocculating colloid in this one-step test indicates the presence of a polymer-destroying protease.

An Unprotected-Sensitizing Example

Sucrose is a small (formula weight 340) uncharged disaccharide which is a substrate for certain enzymes which catalyze sucrose through polymerization into polysaccharides having a formula weight frequently exceeding one million. Sucrose itself is not a colloidal protector or a sensitizer, but the synthesized polysaccharides can be. Thus when the enzyme from mutans streptococci is incubated together with a combination of sucrose, colloidal suspension and nonflocculating concentration of electrolyte-an unprotected condition-flocculation occurs as a result of the accumulation of a sensitizing amount of enzyme-produced polysaccharide. Flocculating colloid in this one-step test indicates the presence of a synthesizing enzyme.

An Unprotected-Protected Example

When a glucosyl transferase from mutans streptococci is extensively incubated with a solution of sucrose and unprotected colloidal suspension-containing no electrolyte-no flocculation will be observed, despite demonstrated production of polysaccharide-i.e., turbidity, When a solution of an ordinarily flocculating (to the unprotected sucrose and colloidal suspension) amount of electrolyte is added to this reacted mixture, the colloid fails to flocculate, indicating a protective action by synthesized polymer. Thus, in this multiple-step test, the presence of a polymer-synthesizing enzyme is indicated by a failure to flocculate upon electrolyte addition, while an absence of enzyme action results in a flocculation.

An application of the phenomenon of protection has been used by physicians and clinics (Lab Manual of Colloid Chemistry: Holmes Harry, 1934) as the "gold number" of cerebrospinal fluid in the diagnosis of certain diseases, as there were found to be protective agents-later found to be excess levels of proteins-in the fluid of diseased individuals compared to healthy individuals.

SUMMARY OF THE INVENTION

It is an object of the invention to provide means to measure small amounts of enzyme activity with a visibly apparent result.

It is an advantage of the present invention that detection of a hydrolytic enzyme may be provided by a single-step technique.

It is a further advantage of the present invention that biological samples such as blood, serum, urine, etc., are acceptable samples in the performance of the present invention.

It is a further advantage of the present invention that the result of the detection is a visible color change.

It is a further advantage of the present invention that the sensitivity of detection for protease enzymes is very high.

A further advantage of the present invention is that in many embodiments, a virtually instantaneous result is provided. In other embodiments, rapid detection is provided.

A feature of the present invention is that any of a variety of hydrolytic enzymes may be detected in accordance therewith, by providing an appropriate substrate for the enzyme to be detected.

Another feature of the present invention is that the natural substrate of the enzyme to be detected is employed. In many instances such a test is more reliable than a test using a synthetic analog or a substrate that is "tagged" with a "reporter" substance.

It is a feature of this present invention that by adjusting the ratio of or polymer to colloid above the sensitizing (optimal) level, detection limits for hydrolyzing enzymes can be specified as needed from very sensitive to less sensitive.

Another embodiment of this invention is the substitution of a synthesized polymer for a natural substrate in such instances wherein improvements in specificity of the desired enzyme activity is required. If only trypsin activity is desired to be measured from a mixture of general proteases, the synthetic polymer poly-lysine-arginine substituting for gelatin would select trypsin activity and not others based on its known cleavage specificity for arginine and lysine redidues.

An additional feature of the present invention is that it can be adapted for other hydrolytic cleaving enzymes that cause a digestion of a polymer to smaller units which include enzymes other than those which cleave peptide bonds, for example, those which cleave esters, and glycosidic bonds.

An optional feature of the present invention involves the use of a carrier protein, coated onto the colloidal particles that serve as detection agents, which improves the specificity of the test and minimizes the amount of (often expensive) specific protein substrate used in the test. [Like for example gelatin as a carrier protein and human type I collagen at $3000/g the true substrate].

An additional feature of the present invention is that it is adaptable to detect enzymes that form proteins or other polymers, such as polysaccharides, for example.

A particular feature of this invention is that synthesizing enzymes in the presence of a colloidal dispersion will serve to protect the dispersion from normally flocculating additions of electrolyte through the production of proteins or other polymers.

A particular embodiment of the present invention used to detect enzymes that form polymers is a two-portion method, which has an advantage of enhanced sensitivity of detection.

An alternative embodiment of the present invention permits measurement and detection of enzymes responsible for the construction of polymeric products from small monomeric or oligomeric substrates.

In some embodiments of the invention, the colloid is an organic dye. In others, the colloid is a finely dispersed metal.

In preferred embodiments of the invention, a specific color change is the detectable event, e.g. red-to-orange or red-to-blue.

An additional advantage of certain embodiments of the present invention is that specificity of the test may be enhanced by selecting a specific colloidal dye of other flocculating agent based on its optimal pH for flocculating.

The present invention is applicable to the measurement and detection of enzymes which produce the destruction, the depolymerization, or the partial cleavage of a polymeric substrate. The measurement may be quantitated using an instrumental monitor. The present invention employs a "natural" substrate for a hydrolytic enzyme of interest (e.g., gelatin for the gelatinase class of enzymes, collagen for collagenase, and so on) and may achieve rapid speed. The present invention may be performed using a biologically-derived sample for diagnostically relevant purposes.

Alternatively if a protein-forming enzyme is introduced into an aqueous system containing protein precursors, the buildup of protein by enzymatic synthesis would achieve the ability to sensitize a colloid that is present in the system. The change from colloid to floc is a result of a sensitizing, that is lower than protecting, buildup of adsorbed polymer produced from enzymatic synthesis in the presence of not normally flocculating ionic strength. This invention accordingly measures an enzyme activity specific for destroying (or synthesizing) the polymer adsorbing to the colloid.

DETAILED DESCRIPTION

Visible Result

A dispersion of colloidal particles in liquid is called a "sol." Some sols appear to possess a color; for example, colloidal gold sols may appear red, orange or purple depending upon the size of their monodisperse particles. Colloidal dyes such as the Congo-type appear red and orange when suspended. When dispersed particles are aggregated with the addition of electrolyte, the perceived color of the dispersion changes depending upon the degree of aggregation. This characteristic is based on the change in reflection and transmission of the light falling on the dispersion, and is easily detected by eye.

Colloids, in addition to the aforementioned colloidal gold sols and the Congo dyes, which may be substituted in the practice of the present invention include, for example, inorganic colloids such as: silver iodide, silver bromide, copper hydrous oxide, iron oxide, iron hydroxide, or hydrous oxide, aluminum hydroxide or hydrous oxide, chromium hydroxide or hydrous oxide, vanadium oxide, arsenic sulphide, manganese hydroxide, lead sulphide, mercury sulphide, barium sulphate, titanium dioxide, bentonite, and clay (U.S. Pat. No. 4,313,734). Also, they include organic colloids such as: night-blue sol, benzoin purple sols, alkali blue sol, Orange II, benzopurine 4B, Bordeaux extra, dismine violet N, azo-blue, Chicago blue 6B, polystyrene latex, Direct Fast Orange SE, Solway Ultra Blue B, and Chlorazol Sky Blue FF.

Sensitivity

I found that minute quantities of trypsin lower the shielding and protecting action of gelatin added to a colloid. By virtue of its endoproteinase activity, i.e., the enzyme's ability to cleave the extended polypeptide chain at multiple sites throughout its length, it destroys the physical-chemical barrier to salt-induced flocculation. When the gelatin present in the system falls below a certain level as it is destroyed by the trypsin, the colloid flocculates-as it becomes instantaneously susceptible to the color-changing action induced by the salt.

Because the gelatin is in alight excess in the protection mode and is physically and irreversibly adsorbed to the colloid's surfaces, no other polymer added afterwards can perturb the system, like for example small amounts of added protein or nonspecific polymers found in a biological sample. This improves the selectivity of the measurement.

Previous studies of colloid-gelatin adsorption show that gelatin is bound tightly to the surface, e.g., with silver bromide (Kragh), and silica, quartz (Kraugh and Langston) and gold sols (Zsigmondy, 1917).

For example, only 16 per cent of gelatin is able to be desorbed from silver bromide colloid (Kraugh and Peacock) at sensitizing concentrations, though only a small portion of the molecule is physically adsorbed to the charged colloidal surface. The major portion of the length of the polypeptide chain extends unadsorbed in a random coil from the surface in loops. The thickness of a layer of gelatin adsorbed to the surface of silver bromide was of the order of 50 nm root mean square (Wood, et. al.). Others have found evidence of a similar thickness for adsorbed gelatin on glass (in Wood and Courts). These loops can interact intermolecularly with other extended loops of gelatin chains on the surface of the same or a different colloidal particle. This interaction causes protection when the gelatin is adsorbed to capacity, disallowing close approaches and collisions of the colloid particles, which would otherwise result in flocculation.

Gelatin protection: Zsigmondy in 1901 showed that when sufficient gelatin was present, a protective action upon salt flocculation of colloidal gold was obtained. Among a number of naturally occurring substances investigated, gelatin proved to be the finest protectant. Theoretical as well as subsequent electrokinetic and tryptic digestion experiments revealed that gelatin bound irreversibly to the surface of the particles in a monolayer and since the mean average diameter of the layer proved to be larger than the smallest diameter of the molecule in solution, the adsorption occurred not as flat sheets, but as looped structures in which some spots are anchored and others free. This is referred to as the VW adsorption, the points of the "V" and "W" are anchored.

This depiction also is helpful for explaining sensitization, as the small number of extended loops in this condition, smaller than the case with protection, would improve the chances of colloid-colloid interaction. Such polymeric loops would extend within the stabilizing charged double layer surrounding the colloidal surface, a situation in which flocculating conditions are improved as a result of bridging between intermolecularly separate gelatin loops.

I analyzed the potentially susceptible cleavage sites within the gelatin protein chain. The literature reveals that bovine alpha I gelatin contains 8% arginine and lysine residues. It is conceivable in theory that as few as two well placed cleavages-one each beside each of the irreversibly adsorbed two ends of the polypeptide, thereby removing the extended loop-could sensitize or return the colloid to an unprotected state by destroying the protection afforded by the extended loop, resulting in aggregation.

A further reason for the high sensitivity of the present invention is due to the small difference between the concentration of gelatin that provides protection and the concentration that provides sensitization. I have experimentally determined that just 300 micrograms of gelatin (or approximately 3 nanomoles for 95,000 mw gelatin) for each milligrain of colloid demarcates the change between protection and sensitization of colloidal gold. This corresponds to a maximum substrate concentration ($S_{max}$) in the kinetic analysis of the enzyme action. It is noteworthy that in actual application, 1/50th of a milligram of this colloid is used, so at most, 6 micrograms of gelatin (or approximately 93 picomoles) need to be destroyed or otherwise inactivated to produce the color change due to flocculation. This results in excellent sensitivity compared to current techiques.

Natural Substrate

This invention incorporates into its action the proper substrate of the enzyme of interest. In the quest to detect and measure clinically important enzymes, investigators have reverted to employing various synthetic substrates containing reporter groups, such as radionuclides or chromophores (such as p-nitrophenol) as conveniences.

For example, trypsin enzyme activity can conventionally be followed by measuring the rate of release of the yellow chromophore p-nitroaniline using the synthetic substrate N-alpha benzoyl-L-arginine p-nitroanilide.HCl (BAPNA). But when dealing with a biologically diverse mixture, positive results using this substrate can be referred to as "trypsin-like", an ambiguous term which suggests more than one possible enzyme activity.

The literature reports instances in which enzymes in a biological specimen are active on synthetic substrates but possess no action toward the natural substrates upon which the synthetic version is based. This is an example of low specificity. Thus, Uitto (1987) detected a large amount of elastase-like and plasmin-like activity in human gingival (gum) tissue using supposedly specific synthetic analogues of the substrates elastin and fibrin, respectively, but no activity was noted upon prolonged contact with the natural substrate dispersed and detectable by staining within an agarose gel. Thus, elastase-like and plasmin-like activity are not as distinctive for measuring the factors responsible for the destruction of the actual tissue components in vivo, placing in question the utility of such a test using these synthetic substrates for a diagnostic decision.

Other examples of low specificity of synthetic substrates in the literature include enzyme activity profiles of *Treponema denticola* capable of hydrolysis of PLGPA, (phenylazobenzyloxycarbonyl-L-prolyl-L-leucylglycyl-L-prolyl-D-arginine, a purported synthetic collagenase (regarded as an endopeptidase) substrate, yet no strain showed measurable hydrolysis of elastin-orcein, azocoll, and serum albumin (Makinen, et al., 1986).

Assay systems employing synthetic substrates have also proved inconvenient due to the fact that enzymes bound to their specific inhibitors are still capable of hydrolyzing small synthetic substrates (Kasten et al). For this reason, the most reliable method for measuring these enzymes particularly in biological samples is to employ the native enzyme substrate.

When using a natural substrate in accordance with the present invention, it is important to address the issue of specificity. Some enzymes possess an apparent general activity regarding a protein substrate. Thus trypsin can hydrolyse many different proteins containing arginine and lysine residues. Indeed trypsin does digest gelatin most readily. However, other general proteases, working differently at different residues-for example chymotrypsin, bromelain, pepsin, and papain-are also capable of hydrolysing gelatin. So the term "gelatinase activity" is possessed by all these proteinases and more.

By providing a polymer specific for the enzyme of interest, this invention is capable of detecting and measuring any hydrolytic enzyme of interest. Thus, if a polymer of lysine and arginine (poly-LysArg) were substituted for gelatin in the above example, only trypsin would act upon this substrate; the other proteases would show no change.

But certain enzymes which act specifically upon only a certain area within one polymeric substrate can be detected and measured specifically by the technique of the present invention, which improves the confidence of the diagnostic measurement. This is the situation with the collagen-vertebrate collagenase measurement. Only vertebrate collagenase cleaves at a particular point within the structure of the substrate. Bacterial collagenase, on the other hand, cleaves collagen in a manner similar to the way trypsin cleaves gelatin. Because actual collagen is used as a substrate, the test of the present invention is specific for a collagenase activity. This is unlike PLGPA, which does react with collagenase but also with other endopeptidases as well, and thus could result in "false positives" in the presence of such endopeptidases.

Other possible substrates which may be employed in the present invention to detect the associated enzyme of destruction are listed in Table 1.

One way to make a test truly specific for a particular enzyme would be to tailor a polymer to a specification and/or add to the reaction inhibitors of other enzymes so that only the desirable one is reactive. For example, in the case of the gelatinase class of enzymes, all of the proteases listed cause colloidal flocculaton of the protective action by destroying the gelatin backbone, but as mentioned, in different ways, because gelatin contains a mixture of amino acid residues which are cleavable by a variety of proteases. If one substituted for gelatin a random colpolymer of, for example L-lysine and L-alanine, molecular weight 50,000 to 150,000, only trypsin, out of the examples given, can cleave this polymer; all others mentioned cannot. Similarly, there is commercially available a polymer of Glu-Ala, which will be sensitive to the action of *Stapylococcus aureus* protease, which cleaves on the —COOH side of Asp and Glu. In this case one can tailor the polymer to fit the specificity of the desired protease.

TABLE 1

| Polymer | Enzyme |
|---|---|
| IgM, IgA, IgG | Specific and Non-specific Ig proteases |
| mucopolysaccarides | hyaluronidase |
| glycogen | glucan phosphorylase |
| polyribonucleotides(polyA, etc.) | phosphorylases |
| RNA | ribonucleases |
| pectin | pectinase |
| DNA | deoxyribonuclease |
| starch | amylase |
| soluble cellulose | cellulases |
| dextran | dextranase |
| mucopolysaccharide | lysozyme |
| casein | general proteases |
| elastin | elastase |
| collagen | collagenase |
| fibrin | plasmin |
| tannin | tannin hydrolases |
| gum arabic, all gums | gum hydrolases |
| alginic acid | alginic acid hydrolase |
| bovine serum albumin (BSA) | general proteases |

Rapidity

The fast speed of the test is due to the cascade nature and "cocked trigger" action inherent in the chemical system of the present invention. There are both an active and a passive element to the working of the test. First, the action of enzyme upon the small amount of substrate is the one active element responsible for the speed of the result. In theory, as described above in the section headed SENSITIVITY, just a small number of cleavages are required by a hydrolytic protease to deliver a positive result.

The system of the present invention may be contrasted to a test based on the solubilization of a diazo dye-coupled insoluble collagen substrate, azocoll (Chavira et al.) in which case many more cleavages are required to release labeled fragments which can be quantified spectrophotometrically. Azocoll, despite being manufactured from insoluble collagen, is degraded by a variety of enzymes, is inconvenient to aliquot because it is insoluble, may require extensive pre-washing to remove inhibitory substances, and requires vigorous agitation to obtain maximum hydrolysis.

Following this active portion, a passive element—the flocculation of the colloid as the detector event—is in most cases an instantaneous event. This is especially so when colloidal metals are used. The flocculation occurs without any other steps or manipulations. These two elements combine to produce a rapid measurement.

Biological Sample

All of the mentioned advantages and characteristics of the present invention combine to allow in aiding the diagnosis of disease using a biological sample. Prior assays for specific proteases tend to be complicated and costly and are better suited for research than for clinical use. The nature of the protective concentration of the polymer prevents nonspecific adsorption of any other polymer in the sample, and the specificity of the natural substrate confers confidence in the result.

In addition, the speed and sensitivity of the present invention allows rapid measurements of physiological processes which might otherwise be missed using conventional techniques. Many physiological processes are under tight metabolic control mechanisms. The manifestation of disease is sometimes a result of the elimination of these controls, a result of an imbalance of controls.

As an important clinical example, the degradation of collagen in destructive periodontal disease which results sometimes in tooth loss has many elements of control, from the rate of synthesis and degradation of collagen to its destruction rate. Furthermore these elements are under control as, for example, specific inhibitors in plasma and gingival fluid, such as tissue inhibitors of metalloproteins (TIMPs), and alpha 2-macroglobulin which bind to and prevent destructive enzymes from exerting their action in vivo. Also vertebrate collagenase is secreted in an inactive proenzyme form which must be activated through several known mechanisms, such as proteolytic cleavage of a part of its structure to activation by thiol-containing activators, to become active. One theory suggests that net collagen destruction is evident as a result of the release from inhibition of active collagenase and other metalloproteases such as gelatinase (Uitto, et al., 1987, 1990). It is the imbalance of the intricate control processes which cause destructive periodontal disease.

In measuring the action of collagen breakdown using a biologically derived sample, the measurement ideally is a freeze-frame of what is suspected to occur in vivo at the time of the sampling. Alterations in the measurement, and hence the degree of confidence in the result, could be introduced by the conditions of measurement. Thus, in the stated case, if the duration of the test is excessive and/or delay in the time of measurement too long, the results will not reflect the true nature of the enzyme activity in vivo. For example, generalized proteases present in the sample might cleave inactive procollagenase into its active form during that time, producing a measurement which is not representative of the in vivo situation. The present invention, because it is rapid, uses a natural substrate and can use a biological sample, avoids these potential interferences from yielding a diagnostically reliable result.

Polymer-Forming Enzymes

The overall concept of the present invention is also applicable to the reverse situation, that of measuring enzyme activity responsible for the synthesis, instead of the cleaving, of polymers from simple precursors or monomers. In one example of this reverse application, very small amounts of polysaccharide-a glucan or levan-were measured as a result of synthesis by glucosyl and fructosyl transferases from the disaccharide sucrose by a streptococcal species associated with plaque production and with caries risk. Other examples of enzymes that can be detected in this manner include DNA and RNA polymerases, viral reverse transcriptases, and glycogen synthase.

The Two-Portion Method

A preferred embodiment of the test of the present invention which is applicable to detecting polymer-synthesizing enzymes involves a "two-portion" method. This method is particularly applicable to measuring small amounts of polymer synthesis and enzyme synthetic activity. It differs from the protection-deprotection variation essentially by eliminating relative high levels of electrolyte for flocculation, substituting instead the sequential addition of untreated, bare colloid to a colloidal suspension previously exposed to polymer. The drawback to this methodology is that it is neccessarily a multistep process. According to the empirically derived theory first expressed by Fleer and Lyklema, flocculation will occur under these conditions provided that the amount of polymer added to the first part is sufficient to just completely coat the first portion of colloid, that is, a colloidally-sensitizing concentration of polymer. (In contrast, the protection-deprotection method contains a slight excess of polymer, mandatory for preventing premature flocculation by the electrolyte contained in the mixture). Because the sensitizing concentration of any polymer is less than its protecting quantity, this two-portion technique allows greater detectability of the polymer and polymer synthesis than the other protecting method. This allows for a greater dilution of any incubating mixture-a step which serves to eliminate contaminating and interfering unspecific polymers in the sample. This method is also useful as a way to insure optimal coverage of any polymer adsorbing onto colloidal surfaces.

Two-Portion Method of Flocculation

Water soluble polyvinyl alcohol, molecular weight 10,000, and dextran from Leuconostoc mesentroides, molecular weight 10,000 were assessed for their ability to flocculate colloidal gold sol using the two portion method. One-half milliliter of gold sol (0.01%) is added to 1.66 milliliters of 10 Mm KCl, followed by 0.66 ml of diluted polymer in distilled water. This was incubated for 30 minutes at room temperature followed by the addition of another one half ml of colloidal gold. The results are found in Table 1A:

TABLE 1A

| Concentration of Polymer per ml | | | | | | |
|---|---|---|---|---|---|---|
| 1 mg | 100 μg | 10 μg | 1 μg | 0.1 μg | 0.01 μg | 0 |
| Flocculation | | | | | | |
| PVA − | − | − | − | + | + | − |
| Dextran − | − | − | − | − | − | − |

PVA, a branched uncharged polymer caused colloidal gold to flocculate in the range between 66 and 666 ng per mg of gold sol by the two portion method. In contrast, straight chain uncharged dextran polymer of the same size did not.

Specific applications for the present invention include, for example:

1. Using a saliva or subgingival plaque specimen, instantaneously measuring destructive enzymes responsible for active periodontal disease. Gelatin or collagen substrates are used for measuring gelatinase or collagenase, known to be present in healthy oral fluids but significantly elevated in those suffering from destructive periodontal disease, sometimes resulting in a loss of teeth.

2. Using a tissue biopsy, detecting polymorphonuclear elastase to aid the diagnosis of breast cancer malignancy. It has been suggested that proteolytic enzymes may play a pathogenic role in the spreading of cancer. Polymorphonuclear elastase was found in 89% of 323 tumor sample of breast carcinoma, and not detected in 10 normal biopsies [Van Der Auwera, P., Feverly, D, LeClerq, O, Bonnet, M, Vifquin, L. PMN-Elastase is expressed by Malignant Cells of Breast Carcinoma but not by Normal Breast Tissue. *Clinical Chem* 34: 1295 (1988)]. Current techniques use an indirect immunoassay for this measurement.

3. Using tissue biopsy, measuring the activity of collagenase to correlate with the metastatic potential of skin cancer. Collagenase levels in one study were found to be 9 times higher in squamous cell carcinoma compared to basal cell epithelioma and seborrheic keratosis [Tsuboi, R. et al, Comparison of Proteinase activities in squamous cell carcinoma, basal cell epithelioma, and seborrheic keratosis. *Journal of Investigative Dermatology* 90: 869–872 (1988)].

4. Using washed spermatozoa, measuring acrogin, a serine protease partially responsible for gamete fusion (fertility) by virtue of its drilling action on zona pellucida surrounding the ovum. Current methods involve using a small synthetic substrate. The present invention utilizes a gelatinase substrate which is digested by acrosin in vivo.

5. Using amniotic fluid, measuring the activity of acid protease. This enzyme has been assigned a predictive value in assessing fetal lung maturity and incidence of respiratory distress syndrome. [Menashe, M. et al. Amniotic fluid protease activity, protease inhibitory activity, and fetal lung maturity. *American Journal of Perinatology* 4: 68–71 (1987)].

The following examples describe in detail various means and methods for carrying out tests embodying various aspects of the present invention. It will be apparent to those skilled in the art that many modifications, both of materials and methods, may be practiced without departing from the purpose and intent of the present invention.

EXAMPLE 1

Congo Rubin

I have utilized a series of direct dyes of the Congo type which possess colloidal behavior in aqueous suspension. This behavior is due in part to their elongated hydrophobic shape and a fixed negative charges. Aggregates are formed due to the Van der Waals interactions of the hydrophobic portion tending to attract, while coulombic actions tend to repel. Despite a small molecular size-about 700-the dyes behave like large particle suspensions. They are further aggregated by electrolyte action and adsorb polymers, proteins, and enzymes with maintenance of activity.

Colloidal Dye and Adsorbed Gelatin

These experiments used Congo Rubin, Type I gelatin (Sigma Chemical, acid-cured porcine skin, approximately 300 Bloom), and 10% sodium chloride in water.

Protective Concentration of Gelatin: Critical Protective Concentration

A solution of gelatin was prepared by melting 100 mg/10 ml at 40° C. Dilutions of this were prepared in water and 0.1 ml of each dilution was added to successive wells of a row of a microtiter plate. To these was added 50 microliters of 1 mg/ml of Congo Rubin and then allowed to incubate for 1 hour. Next, 50 microliters of 10% sodium chloride was added and mixed. The color of the Congo dye was assessed as red (unflocculated) or orange (flocculated) immediately. Table 2 reports the results of these tests.

TABLE 2

| | Concentration of Gelatin, mg/ml | | | | | | | |
|---|---|---|---|---|---|---|---|---|
| 10 | 5 | 2.5 | 1.3 | 0.6 | 0.3 | 0.16 | 0.08 | 0 |
| Flocculation − | − | − | − | − | − | + | + | + |

From this experiment, it was found that reacting Congo Rubin with 0.3 mg/ml and higher concentrations of gelatin protected it from being flocculated by added sodium chloride. Lower concentrations of gelatin did not protect it, and it flocculated, changing color. It is noteworthy that the same pattern of protection was measured using calf skin, bovine skin, alkali processed, with Bloom numbers ranging from 60, 125 and 225. Thus the critical protective concentration ("CPC") is 313 μg gelatin/mg Congo rubin.

The Effect of Trypsin on Gelatin Protection

Fifty microliters of the listed dilutions of trypsin was added to 50 microliters of a 0.6 mg/ml solution of gelatin (final concentration=0.3 mg/ml, the CPC as determined previously) and incubated for 30 minutes at 37° C. Then, Congo Rubin and sodium chloride were added as stated above.

TABLE 3

| | Concentration of Trypsin, ng | | | | | | | |
|---|---|---|---|---|---|---|---|---|
| | 1500 | 750 | 375 | 188 | 96 | 48 | 24 | 0 |
| Flocculation | + | + | + | + | + | + | + | − |

Incubating gelatin with as little as 24 ng of trypsin prevented it from protecting the colloidal dye Congo Rubin from flocculating by electrolyte. Thus, this technique is useful to measure nanogram concentrations of trypsin by virtue of its deprotection action on gelatin.

Absorption Change of Congo Rubin

It was found that the visible color change between Congo Rubin before and after flocculation was capable of being monitored spectrophotometrically. Gelatin-Congo Rubin measured before and after treatment with trypsin showed most differences 505 nm. The red dye has an extinction coefficient of 8990 $M^{-1}cm^{-1}$; upon flocculation, the peak intensity is lowered to 480 nm, and intensity is reduced to 70% of the red dye absorbance at 505 nm.

Kinetic Measurements

The rate of (color) change of absorbance of the trypsin-reacted gelatinase reagent was followed spectrophotometrically by measuring the decrease in absorbance at 505 nm. A plot of the log of the absorbance decrease versus time produced a straight line indicative of first-order reaction rate for the result. From this information, the rate constant, $k = 0.693/t_{\frac{1}{2}}$ was calculated to be 0.14 $min^{-1}$.

RAMIFICATIONS

A. Combined Formulation

It was observed in the study described above that mixing the sodium chloride along with the gelatin prior to adding trypsin had no effect upon the observed results. Furthermore, an experiment was performed to adsorb gelatin onto colloidal dye, then adding salt and producing a "cocked gun" which will "fire" upon addition of protease. This was a nonobvious technological advance because intuitively, it was thought that adsorbed protein would be tightly adsorbed and flattened to the effective surface of the colloidal dye, and that trypsin would be prevented from acting due to unfavorable steric considerations. Pure alpha I 95kD gelatin was substituted for the crude gelatin in previous experiments.

A 1:30 dilution of gelatin, 10 mg/ml was dissolved in 50 Mm sodium carbonate, pH 8.4, then quickly added to 1 mg/ml suspension of Congo Rubin and allowed to adsorb for 1 hour. Sodium chloride was added next. It was discovered that this order of addition is mandatory. This combination is stable for at least 6 months at 8°–10° C. with 0.01% sodium azide added as a preservative.

One part of a solution of the trypsin concentrations listed in Table 4 was added to twenty parts of the gelatin+colloidal dye+sodium chloride reagent described above, and any flocculation by a color change was observed over a period of time.

TABLE 4

| | Trypsin Concentration, ng | | | | |
|---|---|---|---|---|---|
| | 1000 | 100 | 10 | 1 | 0.1 | 0 |
| Flocculation | + | + | + | + | — | — |
| Time to change, hours | 0.3 | 1.5 | 4 | 18 | NA | NA |

The combined formulation produced a stable product which in one step was capable of measuring 1 ng of trypsin.

B. Other Colloids

Other Congo dyes, as appropriate, may be substituted for the Congo Rubin in the formula above. Congo Corinth (Erie garnet) produced a red- to orange-colored result with trypsin and was found to be as sensitive to change as was Congo Rubin, and slightly faster in its response. Congo Red was unresponsive under the conditions stated above; however experiments revealed that this colloidal dye flocculates best under slightly acidic conditions. Therefore, 10 mM sodium phosphate, pH 6.0 was substituted for the carbonate buffer. The results using this was a red-orange to blue color change upon trypsin reaction. Thus in the present invention Congo Red is appropriate for use for those enzymes, e.g. pepsin, that are active under acidic conditions. The selectivity of pH optimum recognized for different enzymes in their catalytic activity combined with the pH response of Congo dyes confers additional specificity to the test.

EXAMPLE 2

Colloidal Gold

Colloidal gold was prepared by the method of Frens in a 50–70 nm size. This preparation was selected because of the true particulate nature of the sol, intense color appearance as well as the consistent size distribution of the particles. The combined formulation of gelatin+colloid+electrolyte was prepared after first determining the critical electrolyte concentration of the preparation, in a way analogous to determining CPC.

TABLE 5

| Determining the CEC of Gold Sol | | | | | | | |
|---|---|---|---|---|---|---|---|
| Concentration of KCl (final) to Colloidal Gold Sol | | | | | | | |
| 1.16 | 0.58 | 0.30 | 0.15 | 0.07 | 0.036 | 0.02 | 0 M |
| Flocculation + | + | + | + | + | + | — | — |

The critical electrolyte concentration for colloidal gold is 0.036M KCl.

Then the CPC for 95 kD gelatin was determined and a protective action was determined at 125 micrograms per mg, compared to 313 micrograms per mg for Congo Rubin.

Specifications and Description of Gelatinase Test

In practice, colloidal gold is titrated with gelatin and salt to produce a stable mixture of polymer-protected colloid. Small volume additions of 1:20 or higher with sample or standard solutions containing protease or gelatinase produce instability to the mixture. Detection limits using purified trypsin approach those obtained using radiolabeled or fluorescent techniques.

Specifications: Gelatinase Test

Colloidal gold concentration: 200 micrograms/ml
Gelatin concentration: 25 micrograms per ml
Buffer: 10 mM Tris HCl, pH 7.4
KCl (electrolyte) concentration: 25 mM
Volume sample: Volume reagent: 1:21
Minimal sample volume: 5 microliters
Detection Limit of Type III Trypsin: 50 ng The detection limit for trypsin using this formulation was 50 ng, approximately 50 times that when Congo Rubin is used. But the result with this colloid was an instantaneous and unmistakable red to blue or clear color change.

Detectability Changes with Colloidal Gold Particle Size

Different size colloidal gold particles produced different sensitivities for gelatinase when formulated in the combined mixture used for measuring enzyme activity in one step. The results are likely due to a surface area change, as the critical polymer concentration differed between the two preparations:

TABLE 6

| | Colloidal Gold Particle Size, nm | |
|---|---|---|
| | 50–70 | >100 |
| COLOR | magenta | purple with yellow Tyndall |
| Critical Gelatin Concentration | 1 microgram/ml | 0.1 microgram/ml |
| Trypsin Detection | 50 ng | 15 ng |

Gelatin Concentration Effect on Trypsin Measurement

A preparation of 40–50 nm particle size colloidal gold was prepared as before. The optimum concentration of gelatin (95% pure 95 kdalton mw Type III bovine) which just completely covered the surface of the particles was determined by the two-portion method. From this study, it was discovered that flocculation occurred in the region of 10 to 20 μg of gelatin optimally coating 1 mg of this preparation of colloidal gold.

A series of preparations having differing proportions of gelatin to colloidal gold was prepared and tested with varying quantities of trypsin in order to determine the detection limits of each. The results indicate that the sensitized preparations are capable of detecting the smallest level of trypsin-63 ng, and that preparations containing higher than sensitizing levels of gelatin added to the gold sol required more trypsin to cause flocculation-up to 500 ng of trypsin or eight times the most sensitive, as the ratio of gelatin to gold was increased from that preparation eight-fold (100 to 800 ng/10 μg).

By manipulating and adjusting these polymer:colloid ratios, the detection limit for detecting enzymes is set to a desired level. This is suitable when applied to those instances where a yes-no cutoff for a particular amount of enzyme is appropriate.

The concentration of sodium chloride used in this study (CEC) was 36.6 mM. Flocculation took place at 25° C. and was instantaneous; a "+" indicates flocculation visually determined as a color change from red to blue-violet; a "—" reflects no color change.

TABLE 7

| | Gelatin: Colloidal Gold Ratio, ng/10 μg | | | | | |
|---|---|---|---|---|---|---|
| | 50 | 100 | 200 | 300 | 400 | 800 |
| Detection Limit of Trypsin, ng | UP | 63 | 125 | 250 | 250 | 500 |

UP = Unprotected infinitesimal sensitivity 100 ng gelatin: Collodal Gold is the CPC as determined by the two-portion method.

EXAMPLE 3

Comparison with Prior Sensitive Assays for Trypsin

As an example of the advantages inherent in this invention, a comparison with two references for measuring trypsin is provided, "A sensitive microplate assay for the detection of proteolytic enzymes using radiolabeled gelatin." [Robertson, B D, Kwan-Lim, G E, Maizels, R M. *Analytical Biochem* 172: 284-287 (1988)] and a "Fluorescein Isothiocyanate-Labelled Casein Assay for Proteolytic Enzymes". [Twining, S S. *Analytical Biochem* 143: 30-34(1984)]

TABLE 8

| COMPARISON BETWEEN ASSAYS | | | |
|---|---|---|---|
| | I125-gelatin | Casein-FITC | Colloidal-Gelatin |
| Incubation Duration | 16 hours | 1 hour | instantaneous-18 hours |
| Steps to result | 2 | 3 | 1 |
| Temperature | 37° C. | 37° C. | 25° C. |
| Linear detection range, trypsin | 1 ng/ml-10 μg | 5-100 ng | 1-50 ng |
| Detector | gamma counter | fluorimeter | visual |

The test of the present invention is as sensitive as current prior art assays for trypsin, is performed at a lower temperature and doesn't require special instruments to measure the results.

Mechanism Confirmed by Gel Electrophoresis

Evidence supporting the theory that the cause of flocculation is a destruction of the protecting effect of gelatin preventing flocculation was obtained by studies using SDS polyacrylamide gel electrophoresis. Two samples of gelatin:colloidal gold:sodium chloride similar to the aforementioned formulation were used.

The first sample was treated with trypsin which had been previously denatured by heating at 100° C. for 5 minutes. The addition of this denatured enzyme did not flocculate the colloid. Another sample was treated with the same amount of active trypsin. This treatment caused the colloid to flocculate in 1.5 minutes. After this, the reacted solution was heated as described to destroy the activity of the enzyme. Each treated reagent as well as gelatin alone was subjected to separation and analysis by SDS PAGE by the method of Laemmli as reported by O'Farrell. Protein bands were detected by staining with Coomasie Blue.

The unflocculated sample produced four protein-stained bands in the regions corresponding to 95, 200 kdaltons and higher kD molecular weight. This same pattern was observed with the gelatin alone. The flocculated active trypsin-treated sample produced no detectable staining pattern, i.e., no protein bands were evident. From this it is concluded that the native structure of gelatin is hydrolyzed to small unstainable polypeptides, and this is the cause of colloidal flocculation.

TESTING FOR ENZYMES IN ORAL FLUIDS

EXAMPLE 4

Collagen and Collagenase

Background: Native collagen is resistant to the action of most proteases, because collagen unlike gelatin possess an ordered structure in which three separate protein chains are wrapped in a triple helical structure, producing a long fibrous polymer. Vertebrate collagenase cleaves collagen specifically across the three chains at one site, producing two segments one-forth and three-fourths the size of the original. In addition this cleaved product is more susceptible to denaturation and action of general proteases, resulting in a further breakdown if these enzymes are present. Thus, vertebrate collagenase only cleaves at one site, whereas general proteases like trypsin on gelatin and bacterial collagenase on collagen can produce hundreds of cleavage products.

Measuring human collagenase and gelatinase in oral fluids is important as an aid in diagnosing periodontal disease as it has been reported that these enzymes originating from the gingival sulcus are found at increased activity levels in salivary and mouthrinse specimens in periodontal diseased individuals compared with healthy individuals. [Gangbar et al. and Uitto, et al., 1990].

The normal assay for collagenase uses a radiolabelled collagen preparation and entails a rigorous treatment of incubations, separations, identification of reaction products and a quantitation which takes three days time and is more suited for research laboratories than clinical chairside and self-administered applications. This invention because of its ease, sensitivity and visible result can be applied to other applications where standard methods prove inadequate.

Collagen-Collagenase

Acid-soluble Type-I collagen (bovine skin from Sigma) was dissolved in 0.5N acetic acid. This was added to dialyzed colloidal gold (removing citric acid which might interfere with the subsequent action of the metal-requiring collagenase) in 10 mM Tris-HCl, pH 7.2, 0.02% sodium azide. The protein was added to just completely cover the particle surfaces as determined by the two-portion method described before. Collagen and colloidal gold were mixed together for 1 hour at room temperature, followed by the addition of an equal amount of bare colloidal gold sol suspension in the two portion method. This was determined to occur at 62.5 microgram of collagen per milligram of colloidal gold. It was also observed in this titration experiment a flocculation without any other addition-a sensatization-occurring at 8 μg collagen per milligram colloidal gold; that is, adding in sequence gold sol, dilute buffer then diluted collagen, (A, below) flocs spontaneously occurred at this dilution of collagen. Adding a second portion of bare gold sol to the mixtures, completing the two-portion method (B, below), complete coverage, as a result of observed flocculation is found with 8 times sensitizing coverage in Table 9:

TABLE 9

| Human Collagen Sensitization and Protection Collagen to Gold Sol, μg/mg | | | | | | | |
|---|---|---|---|---|---|---|---|
| 250 | 125 | 63 | 31 | 15 | 8 | 4 | 0 |
| A — | — | — | — | — | + | — | — |
| B — | — | + | — | — | — | — | — |

Two-hundred microliters of optimally-adsorbed colloidal sol in 10 Mm Tris containing 1 mM calcium chloride was added to an excess (10 micrograms) of trypsin, 3 FALGPA units (1.8 microgram) of clostridipeptidase (collagenase EC 3.4.24.3, devoid of protease activity). After 20 minutes at room temperature, only collagenase produced a color change; excess trypsin did not cause flocculation, nor did an untreated (negative) control. This demonstrates a protected-to-sensitized colloidal flocculation mechanism.

Mechanism Confirmed by Gel Electrophoresis

The mechanism of action of collagenase was studied using SDS PAGE as mentioned previously. Collagenase reagent formulated as above were incubated with trypsin (no flocculation), with collagenase (flocculation), with collagenase without calcium chloride containing added inhibitor, EDTA (no flocculation). Because of numerous impurities in the collagenase preparation, there were multiple silver stained protein bands in the gel preparation; however, only one band at 100 kD corresponded to collagen (alpha1) band because the collagen wall pure. This band was present in the trypsin-containing sample and the collagenase-EDTA sample, but it wall absent in the active collagenase sample. Thus, like the results obtained using gelatin and trypsin, SDS PAGE analysis confirms that the mechanism of flocculating action is due to the destruction of the intregrity of collagen by collagenase enzyme action.

EXAMPLE 5

Caries Diagnostic Aid Enzymes that Produce Extracellular Polysaccharides

*Streptococcus salivarius* is known to produce a water-insoluble dextran—a polymer composed entirely of glucose residues—in addition to a water-soluble levan—a polymer of fructose—produced enzymatically by action of glucosyl and fructosyl transferases, respectively utilizing the substrate sucrose. Some of these extracellular polysaccharides ("ECP's") produced by this species and mutants streptococci are thought to be responsible for initiation of plaque conditions and therefore might be associated with the risk of dental decay (Scheie and Rolla, 1984, 1986).

Measurement of the production of these polymers was performed as follows: Approximately $10^7$ cells in 10 microliters were incubated for one hour at 37° C. in 0.1 ml of 50 Mm sodium acetate, pH 6.2 containing 0.02% sodium azide and 5 microgram per ml of *L. mesenteroides* dextran primer, 10,000 Kd molecular weight and 2% sucrose. As a control, the procedure was repeated in the same reaction conditions with sucrose removed. The reacted contents after this incubation were diluted in 10 mM potassium chloride, and these dilutions were allowed to adsorb onto colloidal gold for 30 minutes, after which another portion of colloidal gold was added to the mixture in the two-portion method of flocculation described previously. In detail, 30 microliters of colloidal gold, 50-70 nm was added to 100 microliters of 10 mM KCl, then 40 microliters of the listed dilutions of *S. salvarius*-reacted sucrose solution and control (without sucrose). After one hour incubation at room temperature, 30 microliters of colloidal gold was added and quickly mixed by vortexing. The results are immediate.

TABLE 10

| | Reciprocal Dilution of *S. salvarius* Reaction | | | | | | | | | | |
|---|---|---|---|---|---|---|---|---|---|---|---|
| | with sucrose | | | | | | | | without sucrose | | |
| | 10 | 20 | 40 | 80 | 100 | 160 | 320 | 1000 | 10 | 100 | 1000 |
| Flocculation | — | — | — | + | + | + | + | — | — | — | — |

*S. salivarius* when incubated with sucrose produced in 60 minutes a product which was able to produce flocculation of colloidal gold using the two-portion method. The equivalent cell sensitivity is calculated to be $1.5 \times 10^5$ to $1.25 \times 10^6$ cells undiluted, producing enough flocculating polymer to cause a positive result. This is a generally accepted range of cells per ml (for mutans streptococci) from cultural studies which indicate a condition favorable for caries development (Scheie and Rolla, 1986).

A Insoluble ECP from mutans streptococci by Direct Flocculation

Dilutions of pure cultures (50 microliters) of ECP-producing microorganisms were incubated in 450 microliters of a solution containing 40% sucrose, 50 mM sodium acetate, pH 6.2 and 0.02% sodium azide for 24 hours at 37° C. Fifty microliters of this was diluted in the above reagent and 100 microliters of colloidal gold, 50-70 nm was then added. No other reagent, gold sol or electrolyte was added.

TABLE 11

| | Cells, thousands | | | | |
|---|---|---|---|---|---|
| | 0 | 75 | 150 | 300 | 600 |
| S. sanguis | — | — | — | — | — |
| A. viscosus | — | — | — | — | — |
| S. salivarius | — | — | — | slight + | + |
| mutans streptococci | — | — | slight + | + | + |

The results indicate that ECPs produced from those oral-species which produce insoluble mutan can directly flocculate gold sol with a sensitivity of approximately 150,000 cells.

EXAMPLE 6

Subgingival Plaque Testing for Gelatinase Using Congo Rubin and Trypsin-like Activity in a Gingivitin Patient Subgingival plaque specimens were obtained by probing the pockets of a patient with gingivitis. The pocket depths at which these samples were obtained were all 3 mm or less (Type I gingivitis). Each sample was diluted in 100 microliter of sodium carbonate buffer, split in two parts with one half added to Congo Rubin-gelatin-sodium chloride gelatinase formulation, while the other was assessed for trypsin-like activity using the synthetic substrate BAPNA. The mixture was incubated for 30 minutes at 37° C. and compared with known concentrations of trypsin. Under these conditions, the gelatinase reagent was able to detect 25 ng of type III trypsin.

TABLE 12

| Gelatinase and Trypsin-Like Activity in Gingivitis | | | |
|---|---|---|---|
| Location | Depth | Gelatinase | BAPNA |
| 4 MB | 3 mm | − <25 ng | − |
| 8 M | 3 mm | − | − |
| 15 M | 3 mm | − | − |

There is no evidence of gelatinase activity or typsin-like activity detectable in three samples from a gingivitis patient.

Subgingival Plaque Testing of Gelatinase Using Congo Rubin and Trypsin-like Activity in Periodontal Disease

TABLE 13

| Gelatinase and Trypsin-Like Activity in Peridontal Subgingival Plaque | | | |
|---|---|---|---|
| Location | Depth | Gelatinase | BAPNA |
| 8 M | 9 mm | +(200 ng) | − |
| 8 DL | 7 mm | − <25 ng | − |
| 14 Furc | 5 mm | +(800 ng) | + |
| 14 M | 3 mm | − | − |
| 25 MD | 3 mm | − | − |

Two locations contained measurable amounts of gelatinase, one of which was positive for trypsin-like activity as well. Thus, these results indicate that the invention is capable of detecting low levels of gelatinase in subginvial plaque specimens in 30 minutes from an individual with periodontitis but not from one with gingivitis. One sample produced a positive result using a natural substrate-gelatin-while trypsin-like activity using a synthetic substrate-BAPNA-was not detected.

Salivary Gelatinase in Periodontal Disease

Gelatinase activity using colloidal gold-gelatin-potassium chloride combined formula disclosed previously was employed to instantaneously detect at least 50 ng of trypsin activity using saliva samples. Saliva was collected first by rinsing the mouth with tap water four times for 15 seconds each, after which any saliva collected in 1 minute was allowed to accumulate but swallowed. Saliva was stimulated by chewing with paraffin and the accumulation collected in a plastic cup at room temperature. The volume and time of collection varied greatly. Ten microliters of each saliva sample, whole and clarified supernatant was added to 200 microliters of the gelatinase reagent and examined for any color change. An aliquot of a sample testing positive was heated quickly in a 75° C. water bath, then tested again to determine the heat lability of the substance responsible for the activity.

TABLE 14

| Salivary Gelatinase Activity | | | |
|---|---|---|---|
| Sample | Disease Class | Comments | Gelatinase |
| A | I-II | pregnant | −whole<br>−supernatant |
| B | IV | female with 10 + mm pockets | +(slight)whole<br>−supernatant |
| C | I-II | 2 × 5 mm pockets | +whole<br>+supernatant<br>−heated |
| D | 0 | supernormal | −whole |
| E | III | missing all maxillary teeth | +whole |

The results indicate that gelatinase can be detected in individuals who have periodontal disease. This activity is heat labile, so the test is not measuring a spurious reaction caused by excess electrolyte or other flocculant in the sample.

Time course of Gelatinase Inactivation

It is known that saliva contains potent inhibitors of enzyme action, specifically for metalloenzymes which can include proteinases like gelatinase, and nonspecific inhibitors such as hydrogen peroxide which destroy activity by virtue of a structural or chemical change. Measuring the activity using this instantaneous gelatinase test of replicate aliquots taken over a period of time of one sample is one way to assess the initial level of activity in addition to the inhibitory action contained within the biological sample.

Saliva was obtained from a Type II (bleeding upon probing with pocket depths > 5 mm) diseased individual and from a normal individual as before. Duplicate ten microliter replicates of the same 5 ml saliva sample were taken and tested by reaction with 200 microliters of gelatinase reagent at successively timed one minute periods through a period of 10 minutes.

TABLE 15

| Loss of Gelatinase Activity Over Time | | | | | | | | | | |
|---|---|---|---|---|---|---|---|---|---|---|
| | TIME, minutes | | | | | | | | | |
| Health Status | 1 | 2 | 3 | 4 | 5 | 6 | 7 | 8 | 9 | 10 |
| Normal | + | + | − | − | − | − | − | − | − | − |
| Class II Perio | + | + | + | + | + | + | − | − | − | − |

The results indicate that gelatinase activity is measurable in the saliva of normal and periodontal subjects using 10 microliters of sample. The activity declines with time in both, disappearing more rapidly with the healthy subject.

Gelatinase Activity of Class II Perio After Treatment

The Class II periodontitis patient underwent oral antimicrobial treatment for this condition and afterwards gelatinase activity of saliva was assessed two weeks after the cessation of therapy. Antimicrobial therapy regime was doxycycline, 3 100-mg doses per day for 3 weeks immediately followed by metronidazole treatment of 4 500-mg capsules per day for 2 weeks. Gelatinase activity was assessed as above, and performed in duplicate. The results are given in Table 16.

TABLE 16

Rate of Saliva Gelatinase Activity Loss
Before and After Treatment

| | TIME, minutes | | | | | | | |
|---|---|---|---|---|---|---|---|---|
| | 0 | 1 | 2 | 3 | 4 | 5 | 6 | 7 |
| Class II Perio | + | + | + | + | + | + | + | − |
| Class II Perio after | + | + | − | − | − | − | − | − |

The results indicate that the rate of gelatinase activity loss in saliva was faster following antimicrobial therapy, and the rate was reduced to that of a healthy subject.

Salivary and Crevicular Fluid Gelatinase Activity

Saliva was collected from a patient with localized Type II and generalized Type I periodontitis. After this, gingival crevicular fluid was collected using paper points from a subset of teeth known as Ramfjord sites which have been proposed as representatives to the estimate of the oral health status within the whole mouth.

| TIME COURSE OF SALIVARY GELATINASE | | | | | | | | | | | | |
|---|---|---|---|---|---|---|---|---|---|---|---|---|
| | 1 | 2 | 3 | 4 | 5 | 6 | 7 | 8 | 9 | 10 | 15 | 20 | 25 |
| Floculation | + | + | + | + | + | + | + | + | + | + | + | − | − |

| GELATINASE ACTIVITY OF CREVICULAR FLUID | | | | | | |
|---|---|---|---|---|---|---|
| | Tooth Location | | | | | |
| | 3 | 18 | 12 | 13 | 28 | 9 | 25 |
| Flocculation | + | + | + | + | + | + | + |

The results indicate that activity is detectable in saliva and its inactivation took place after fifteen minutes. All crevicular fluid samples were positive. The saliva sample reflects the activity exhibited by representative sites of gingival fluid.

Mouth Rinse Sampling for Gelatinase

In an attempt to reduce or eliminate any inhibitors or factors affecting activity in the testing of saliva, a sampling technique using a mouth rinse was tried. Studies have indicated that a mouth rinse can provide an indication of the true contents of the gingival crevicular fluid which though more dilute, will not possess the high concentrations of inhibitors that stimulated saliva carries (Gangbar, et al). one additional reason to attempt this approach is the known observation that trypsin-like enzymes possess optimum activity in 0.1M NaCl and that these proteinases require these high concentrations of salt for their optimal extraction from tissue. This may be attributed to the dissociation of the enzymes from endogenous inhibitors and their natural substrates. The proteinases may also be associated with ionic bonds to other substances such as heparin that binds mast cell proteases in the intracellular granules.

A normal and Class II periodontal patient first rinsed their mouths with tap water as before then after pausing 30 seconds and swallowing any accumulated fluid, swished in their mouth for 30 seconds a 3 ml rinse made with the composition of electrolyte used in preparing the colloidal gold-gelatin test reagent (0.14M sodium chloride). The sample was then added to the colloidal gold-gelatin reagent in the same volume proportion as the normal salt addition, 3 parts colloidal gold-gelatin to one part sample, instead of the one part sample to twenty parts colloidal gold-gelatin-salt reagent as before. Actual volumes were 50 microliters sample plus 150 microliters gelatin-colloidal gold.

TABLE 17

| MOUTH RINSE GELATINASE ACTIVITY OVER TIME | | | | | |
|---|---|---|---|---|---|
| | Time, minutes | | | | |
| | 0 | 10 | 20 | 30 | 90 | 180 |
| Normal | − | − | − | − | − | − |
| Diseased | + | + | + | + | + | − |

The results showed that a rinse contained measurable gelatinase activity in a periodontal diseased subject compared to a healthy subject, and the activity was lost between 90 and 180 minutes compared to losing activity after 7 minutes in saliva.

Kits

It will be apparent to one skilled in the field of such tests that the desirable commercial embodiments of the present invention include the provision of a pre-packaged kit of materials for detecting an enzyme in a sample by the methods set forth above. Such a kit would comprise, for example, a reagent consisting essentially of a colloidal agent that has a flocculated state which is visually distinguishable from its colloidal state, the colloidal agent having adsorbed onto its surface a protective amount of a polymer which is a substrate for the enzyme to be detected, and an additional reagent consisting essentially of an aqueous solution of an electrolyte. Desirably there would also be included a positive control reagent comprising a sample of the enzyme to be detected, and optionally one or more implements useful in performing said test, e.g. a test tube for observing the flocculation.

In such a kit, the colloidal agent is desirably selected from the group consisting of: gold, silver iodide, silver bromide, copper hydrous oxide, iron oxide, iron hydroxide, or hydrous oxide, aluminum hydroxide or hydrous oxide, chromium hydroxide or hydrous oxide, vanadium oxide, arsenic sulphide, manganese hydroxide, lead sulphide, mercury sulphide, barium sulphate, titanium dioxide, bentonite, clay, Congo Red, Congo Rubin, Congo Corinth, night-blue sol, benzoin purple sols, alkali blue sol, Orange II, benzopurine 4B, Bordeaux extra, dismine violet N, azo-blue, Chicago blue 6B, polystyrene latex, Direct Fast Orange SE, Solway Ultra Blue B, and Chlorazol Sky Blue FF.

The enzyme is optionally a member of the group set forth in Table 1 and the substrate is the corresponding polymer set forth in Table 1.

It is to be understood that the invention is not limited to the illustrations described and shown herein, which are merely illustrative of the best modes of carrying out the invention, and which are suitable of modification of form, size, arrangement of steps and details of operation. The invention rather is intended to encompass all such modifications which are within the spirit and scope of the present disclosure, and is defined by the appended claims.

BIBLIOGRAPHY

U.S. Pat. No. 4,164,558. Method for Optimizing Reagents for Agglutination Reactions. Von Schulthess, G K, Cohen, R J, Benedek, G B. Aug. 14, 1979.

U.S. Pat. No. 4,313,734. Leuvering, Johannes H W. Metal Sol particle immunoassay.

Uitto, Veli-Jukka. "Human Gingival Proteases. I. Extraction and Preliminary Characterization of Trypsin-Like and Elastase-Like Enzymes." *Journal of Periodontal Research* 22: 58–63 (1987).

Gangbar, G, Overall, C M, McCulloch, C A G, Sodek, J. "Identification of Polymorphonuclear Leucocyte Collagenase and Gelatinase Activities in Mouthrinse Samples: Correlation with Periodontal Disease Activity in Adult and Juvenile Periodontitis. *J Periodontal Res.* 25: 257–267 (1990).

Fleer, G J, and Lyklema, "J. Polymer adsorption and its Effect on the Stability of Hydrophobic Colloids." *J. Colloid and Interfacial Sci.* 46:(1974).

Uitto, V-J, Suomalainen, K, Sorsa, T. "Salivary Collagenase. Origin, Characteristics, and Relationships to Periodontal Health". *J Periodontal Res* 25: 135–142 (1990).

Uitto, V-J, Tryggvason, K, Sorsa, T. Collagenolytic enzymes in Periodontal Diseases. *Proc. Finn Dent Soc* 83: 119–129 (1987).

Wood, A G and Courts, A, eds. Swelling, adsorption and Photographic Uses of Gelatin in "The Science and Technology of Gelatin" Academic Press, NY, 1977, 441–461.

Scheie, A A, Rolla, G. Polysaccharide Production by Cell Free Transferases in Saliva in Relation to Salivary Microflora. *Scand J Dent Res* 92: 43–49 (1984).

Scheie, A A, Rolla, G. Cell-free Glucosyltransferase in Saliva. *Caries Res.* 20: 344–348(1986).

Buchan, R J, Jenkinson, H F. Glucosyltransferase production by *Streptococcus sanguis* Challis and Comparison with other oral Streptococci. *Oral Microbiol Immunol* 5: 63–71 (1990).

Dibdin, G H and Shellis, R P. "Physical and Biochemical Studies of *Streptococcus mutans* Sediments Suggest New Factors Linking the Cariogenicity of Plaque and its Extracellular Polyeacchride Content." *J Dental Research* 67(6): 890–895 (1988).

Frens, G. Controlled Nucleation for the Regulation of the Particle Size in Monodisperse Gold Suspensions. *Nature Physical Science* 24: 20–22 (1973).

The Chemistry of Colloids Part 1. Zsigmondy, R. John Wiley, Inc. NY (1917).

Kragh, A. M. J. Photographic Sci 12:191 (1964).

Kraugh A. M. Langston, W. B. J. Colloid Sci 17, 101–23 (1962).

Kraugh A. M. and Peacock, R. J. Photogr. Sci 15: 220–5 (1967).

Makinen, K K, Syed, SA, Makinen, P-L, and Loesche, WJ. "Benzoylarginine Peptidase and Iminopeptidase Profiles of Treponema denticola Strains Isolated from the Human Periodontal Pocket" *Current Microbiblocy* 14: 85–89 (1986).

Kasten, M. et al. Anal Biochem 176: 150–156 (1989).

Chavira, R., Burnett, T J, and Hageman, J H. *Anal Bloches* 136: 446–450 (1984).

O'Farrell. J. Biol. Chem 250: 4007–4021].

Ciamasoni, G, and Kowashi, Y "Proteinases of the Gingival Crevice and Their Inhibitors in The Borderland Between Caries and Periodontal Disease II." Academic Press, NY 1980, pp31–49.

Fleer, G J and Lyklema, J. Polymer Adsorption and its Effect on the Stability of Hydrophobic Colloids. II. The Flocculation Process as Studied with the Silver Iodide-Polyvinyl Alcohol System. *J of Colloid and Interfacial Sci.* 16: 1–12 (1971).

I claim:

1. A method for detecting gelatinase in a sample comprising:
   preparing a sol by adding a colloidal protector selected from the gorup consisting of IgM, IgA, IgG, gelatin, casein, elastin, collagen, fibrin and bovine serum albumin (BSA), to colloidal gold to form a protected sol and by further adding a sensitizing amount of sodium chloride to said protected sol where said sensitizing amount is more than the amount required to flocculate said colloidal gold in the absence of the protection provided by said colloidal protector but is less than the amount required to flocculate said colloidal gold in the presence of said colloidal protector; and
   exposing said sol to said sample to flocculate said colloidal gold from a dispersed state to a visually observable flocculated state when gelatinase is present in the sample to thereby visually detect said gelatinase in said sample.

2. The method of claim 1 wherein said exposing step comprises hydrolytically cleaving molecules of said colloidal protector by said gelatinase to expose said colloidal gold to said sensitizing amount of sodium chloride.

3. The method of claim 1 wherein the ratio of said colloidal protector to said colloidal gold is varied to change detection limits for the presence of said gelatinase.

4. The method of claim 1 wherein said colloidal protector is specific to said gelatinase.

5. A method of detecting gelatinase in a sample comprising:
   adding gelatin to colloidal gold to form a protected sol;
   adding a sensitizing amount of sodium chloride to said protected sol where said sensitizing amount is more than the amount required to flocculate said colloidal gold in the absence of the protection provided by said gelatin but is less than the amount required to flocculate said colloidal gold in the presence of said gelatin; and
   contacting said protected sol with said gelatinase to hydrolytically cleave molecules of said gelatin to unprotect said protected sol whereby said colloidal gold in said unprotected sol is flocculated from a dispersed state to a visually observable flocculated state.

6. The method of claim 5 wherein said gelatinase is a destructive enzyme responsible for an active periodontal disease obtained from a saliva, gingival crevicular fluid or a subgingival plaque specimen.

7. A method of detecting collagenase responsible for an active periodontal disease obtained from a saliva, gingival crevicular fluid or a subgingival plaque specimen comprising:
   adding a colloidal protector selected from the group consisting of gelatin and collagen to colloidal gold to form a protected sol;
   adding a sensitizing amount of sodium chloride to said protected sol where said sensitizing amount is more than the amount required to flocculate said colloidal gold in the absence of the protection provided by said colloidal protector but is less than the amount required to flocculate said colloidal gold in the presence of said colloidal protector; and
   contacting said protected sol with said collagenase to hydrolytically cleave molecules of said colloidal protector to unprotect said protected sol whereby said colloidal gold in said unprotected sol is flocculated from a dispersed state to a visually observable flocculated state.

* * * * *